(12) United States Patent
Beavers et al.

(10) Patent No.: US 7,427,290 B1
(45) Date of Patent: Sep. 23, 2008

(54) THERMAL PACK HAVING A COMFORT FIT

(76) Inventors: S. Michael Beavers, 3574 Glyn Caroll Cove, Bartlett, TN (US) 38133; Jed Cowell, 7978 Curlybank Cove, Bartlett, TN (US) 38135

( * ) Notice: Subject to any disclaimer, the term of this patent is extended or adjusted under 35 U.S.C. 154(b) by 118 days.

(21) Appl. No.: 11/151,496

(22) Filed: Jun. 13, 2005

Related U.S. Application Data

(60) Provisional application No. 60/578,989, filed on Jun. 11, 2004.

(51) Int. Cl.
*A61F 7/00* (2006.01)
(52) U.S. Cl. .......................... 607/108; 607/114
(58) Field of Classification Search ................. 607/104, 607/108–112, 114
See application file for complete search history.

(56) References Cited

U.S. PATENT DOCUMENTS 4,854,319 A * 8/1989 Tobin ........................ 607/109
6,409,748 B1 * 6/2002 DeCarlo et al. ............. 607/114
6,435,787 B1 * 8/2002 John ........................... 410/119

* cited by examiner

*Primary Examiner*—Roy D. Gibson
*Assistant Examiner*—Aaron Roane
(74) *Attorney, Agent, or Firm*—Wyatt, Tarrant & Combs, LLP

(57) ABSTRACT

A thermal pack having a bent lip uniformly disposed away from a skin side of the thermal pack. The thermal pack of the present invention eliminates discomfort associated with prior art thermal packs by providing a lip that bends up and away from the skin, thereby avoiding or minimizing contact with the skin and limiting irritation. The pack is preferably provided with an insulated wrap 90 that can be attached to the pack, such as by a hook-and-loop fastener. The wrap will aid in placement of the device upon the user, as well as extend the benefits of the thermal medium. The wrap is conventionally formed of a thermoplastic material commonly used in packaging.

3 Claims, 8 Drawing Sheets

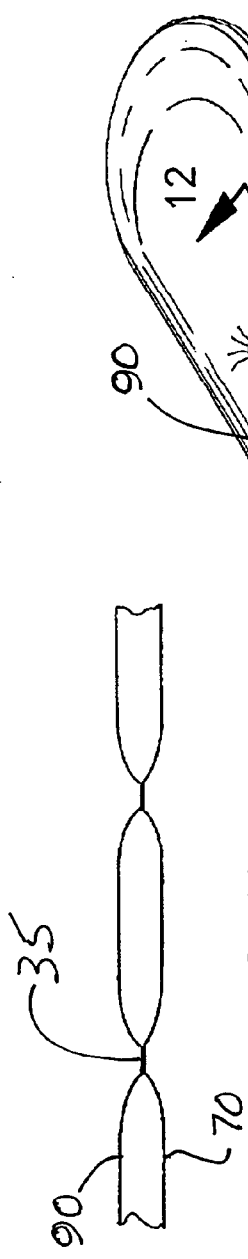
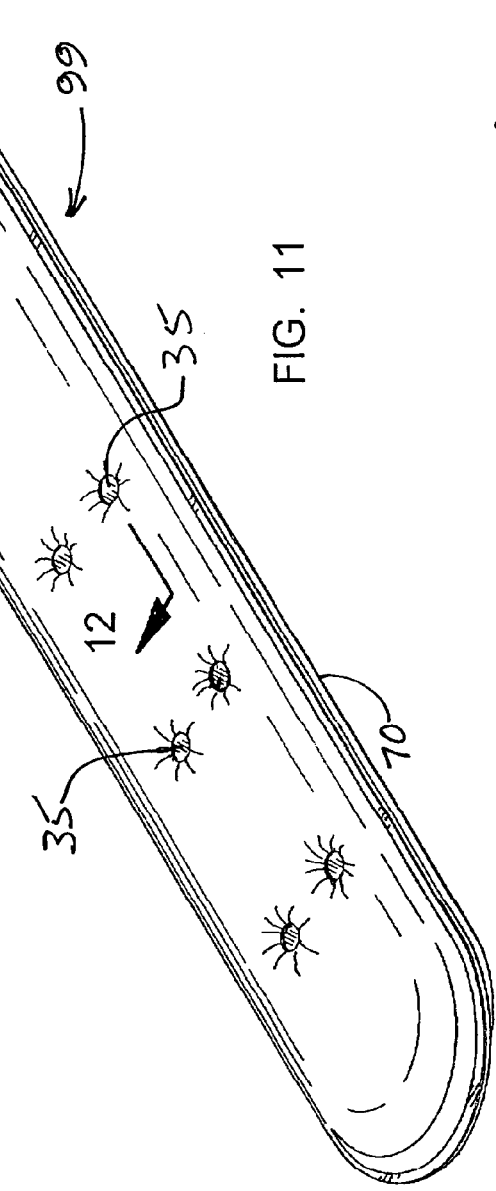
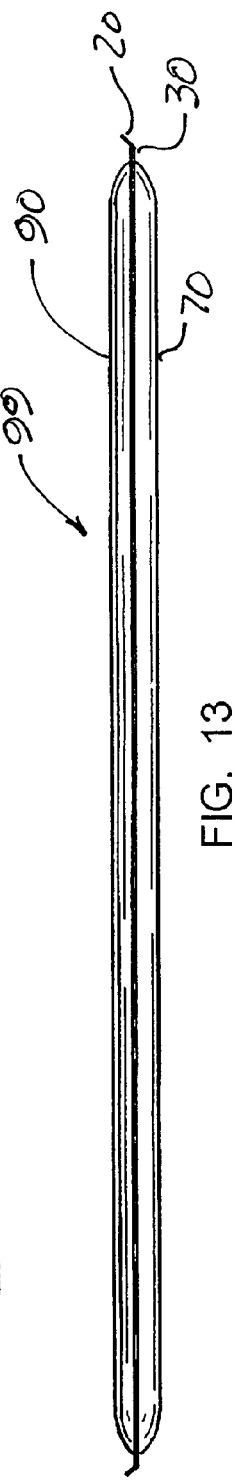
FIG. 11
FIG. 12
FIG. 13

THERMAL PACK HAVING A COMFORT FIT

CROSS REFERENCE TO RELATED APPLICATIONS

This application claims priority of Provisional Application Ser. No. 60/578,989, filed Jun. 11, 2004, the contents of which is fully incorporated herein by reference.

STATEMENT REGARDING FEDERALLY SPONSORED RESEARCH OR DEVELOPMENT

Not applicable

REFERENCE TO A MICROFICHE APPENDIX

Not applicable

FIELD OF THE INVENTION

The present invention relates to thermal packs for use in applying heat or cold to the body of a user, such as in the treatment of injuries.

BACKGROUND OF THE INVENTION

Thermal packs are used for various purposes. Cold thermal packs are used to help control edema (swelling) in human and animal tissue. Cold thermal packs are also used to help control body temperature (cooling vests, cooling collars, hats, etc.). Warming thermal packs are used for medicinal purposes as well as personal comfort.

FIG. 1 shows a prior art thermal pack 5. The thermal pack 5 has two layers or sheets 1, 2, which are joined along a peripheral edge 4 to form a compartment or "bubble" 3 containing thermal material (e.g. ice; chemical mixtures; gels). Commercially available thermal packs are typically manufactured by forming a seal around the periphery of the two layers or sheets 1, 2. This process forms a pack 5 that has a seam or lip 4 that usually extends peripherally and horizontally in the same plane as the seam formed at the junction of the two layers 1, 2, and which runs along the periphery of the pack 5. Because of the thermal process used to seal the pack layers, this peripheral lip 4 often becomes hard, and depending upon the type of material, can feel sharp against the skin. FIG. 2 is a cross-section view illustrating how the peripheral edge 4 of a prior art thermal pack 5 can cause irritation when it comes into contact with the skin of a user. As shown in FIG. 2, when the prior art thermal pack 5 containing thermal material 8 is pressed against the skin 100 of a user, the natural curvature of the skin forces the skin 100 to contact the peripheral edge 4 of the pack 5, causing the skin to be depressed and/or rubbed, and causing irritation at the point of contact 6. Such irritation may cause the wearer to abandon use before the benefits of the thermal pack can be fully experienced.

BRIEF DESCRIPTION OF THE DRAWINGS

FIG. 11 is a perspective view of an alternative embodiment of the invention.

FIG. 12 is a side perspective view of the embodiment of FIG. 11.

FIG. 13 is a partial cross sectional view of the embodiment of FIG. 11 taken along the lines 12-12 of FIG. 11.

PREFERRED EMBODIMENTS OF THE INVENTION

In the following detailed description of the preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the present invention.

Figure 2:
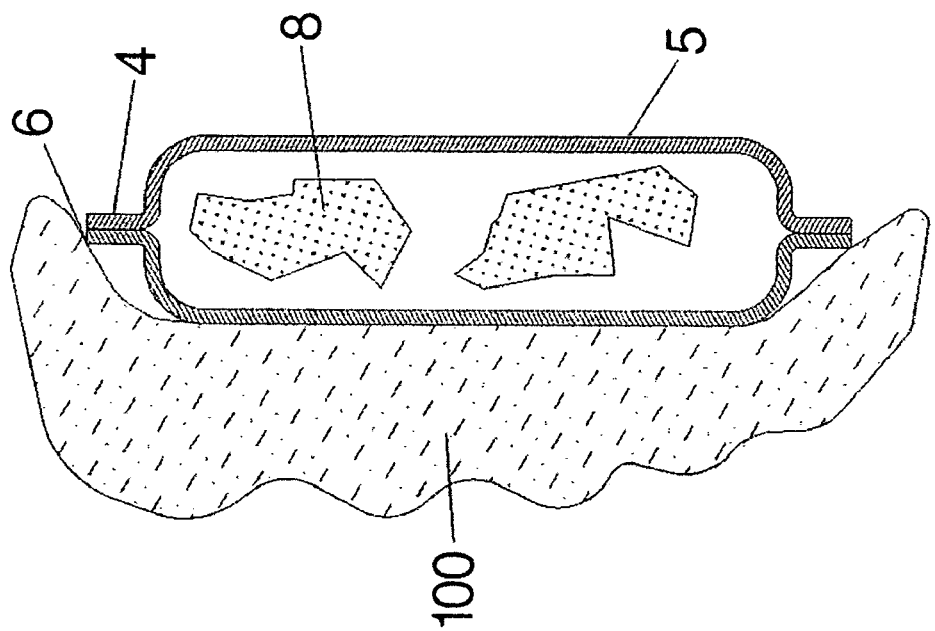
FIG. 2 is a cross-section view of a prior art thermal pack, illustrating how the edges of prior art thermal pack can irritate the skin of a user.
Figure 1:
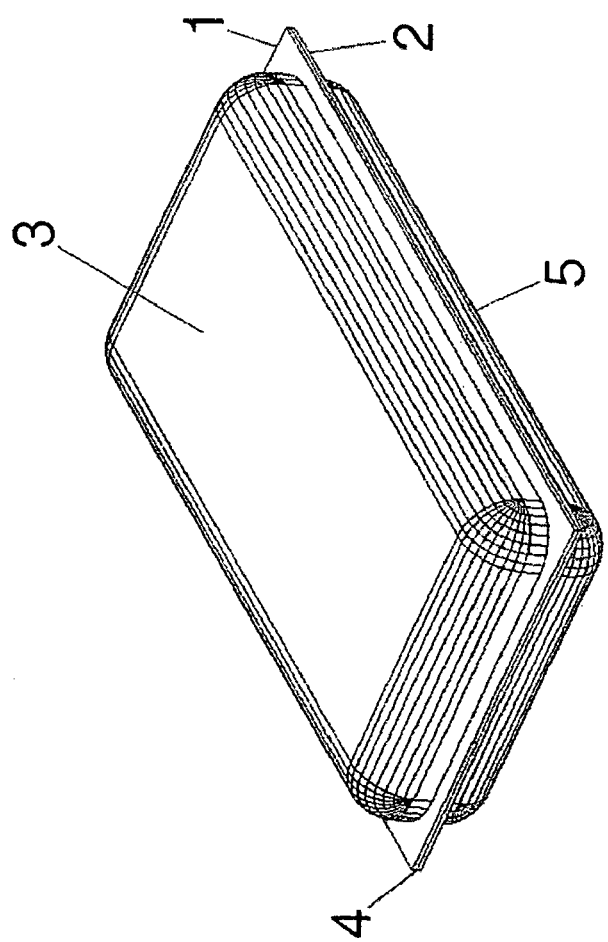
FIG. 1 is a prior art thermal pack.
Figure 5:
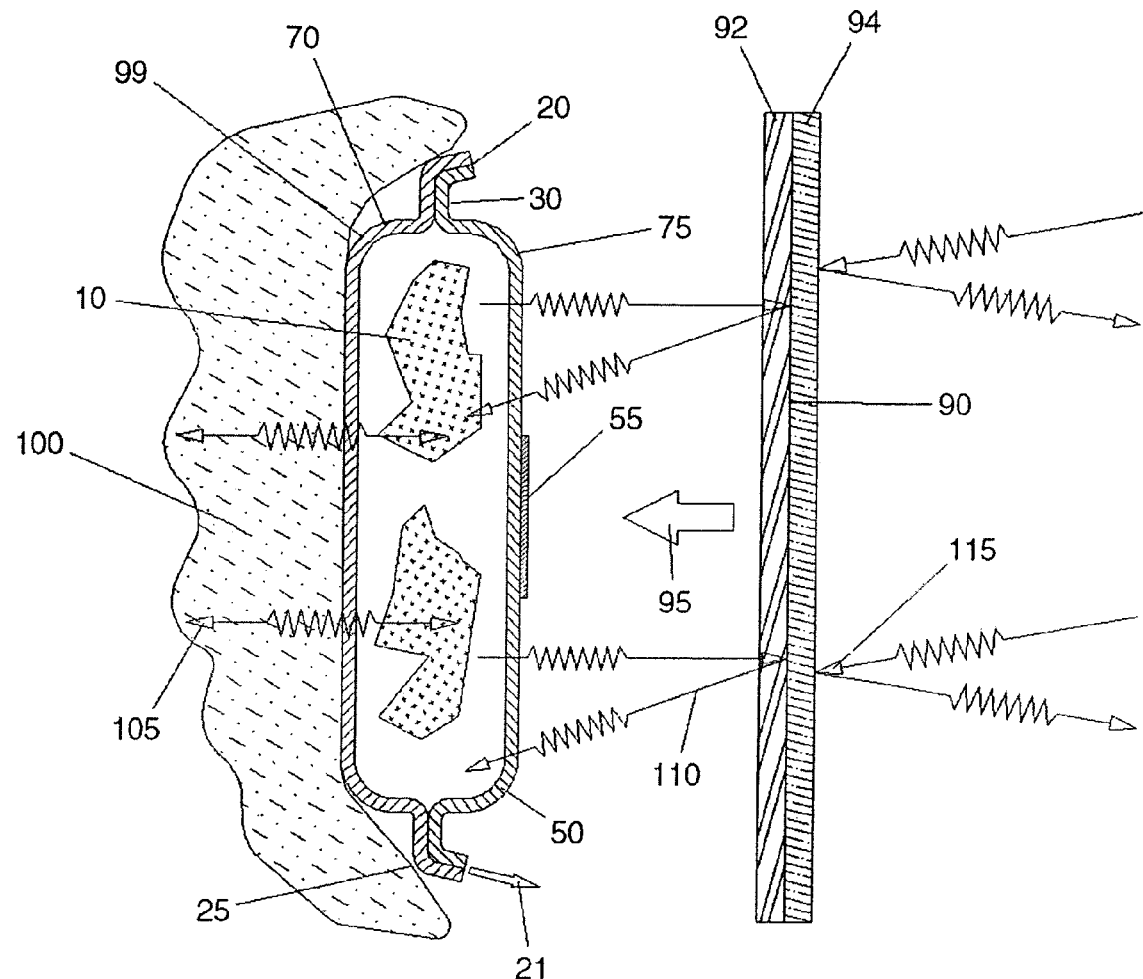
FIG. 5 is a side cross-section view of one preferred embodiment of the thermal pack of the invention, illustrating how the bent lip design avoids irritating the skin of a user, and further illustrating application of a wrap for use in holding the thermal pack in position on a user.
Figure 6:
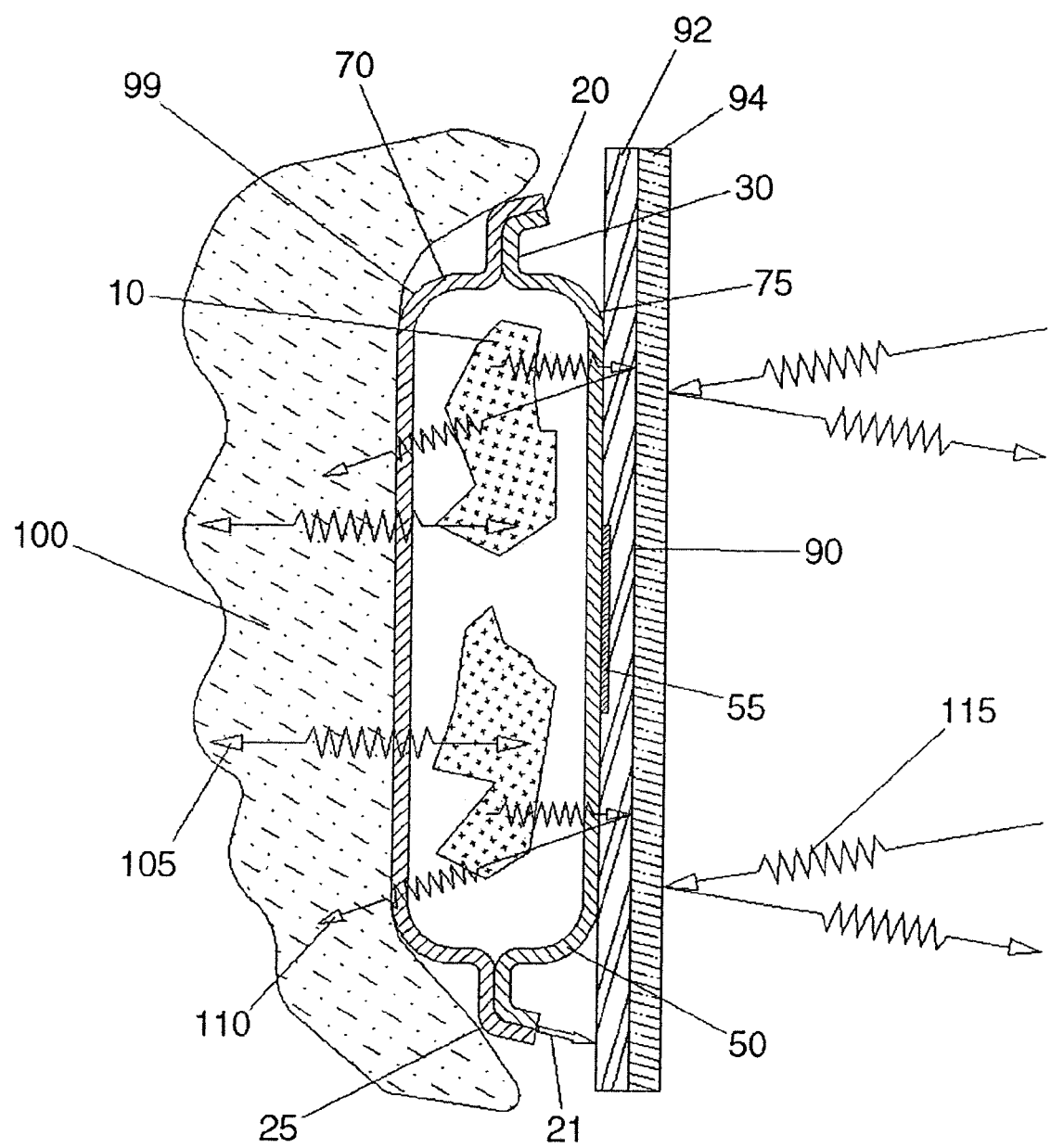
FIG. 6 is a side cross-section view of one preferred embodiment of the thermal pack of the invention, illustrating use of a wrap to maintain the thermal pack in a preferred position on a user.

The thermal pack of the present invention eliminates discomfort associated with prior art thermal packs of the type shown in FIGS. 1-2 by providing a lip that bends up and away from the skin in the area of probable skin contact, thereby avoiding or minimizing contact with the skin and limiting irritation. As shown in FIGS. 5 and 6, the invention is preferably provided with an insulated wrap 90 that can be attached to the pack, such as by a hook-and-loop fastener. The wrap 90 will aid in placement of the device upon the user, as well as extend the benefits of the thermal medium. The wrap 90 is conventionally formed of a thermoplastic material commonly used in packaging. Such materials are formed into containers by known methods, including rf or ultrasonic welding, chemical or mechanical bonding (including adhesives).

Figure 3:
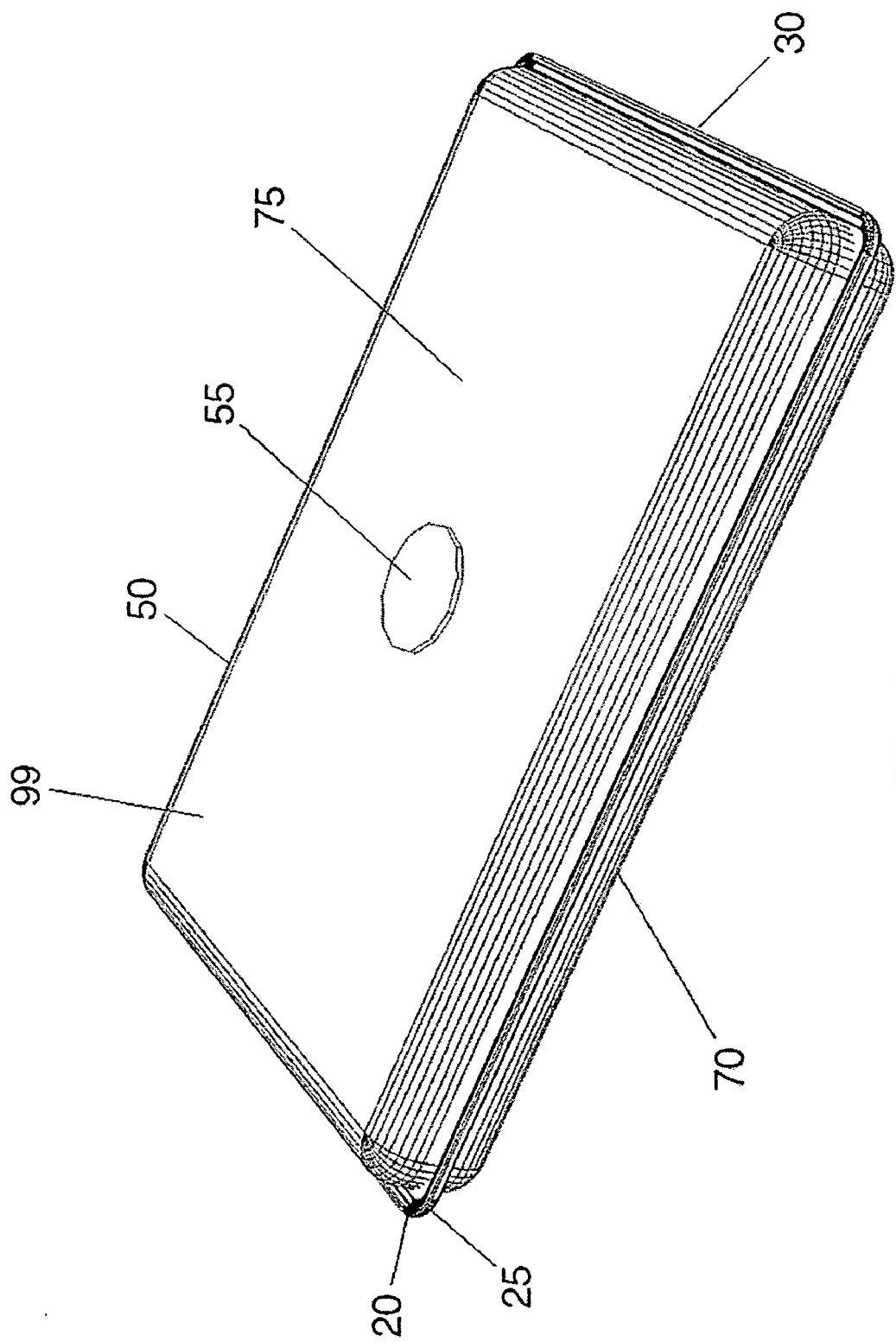
FIG. 3 is a side perspective view of one preferred embodiment of a thermal pack of the invention.
Figure 4:
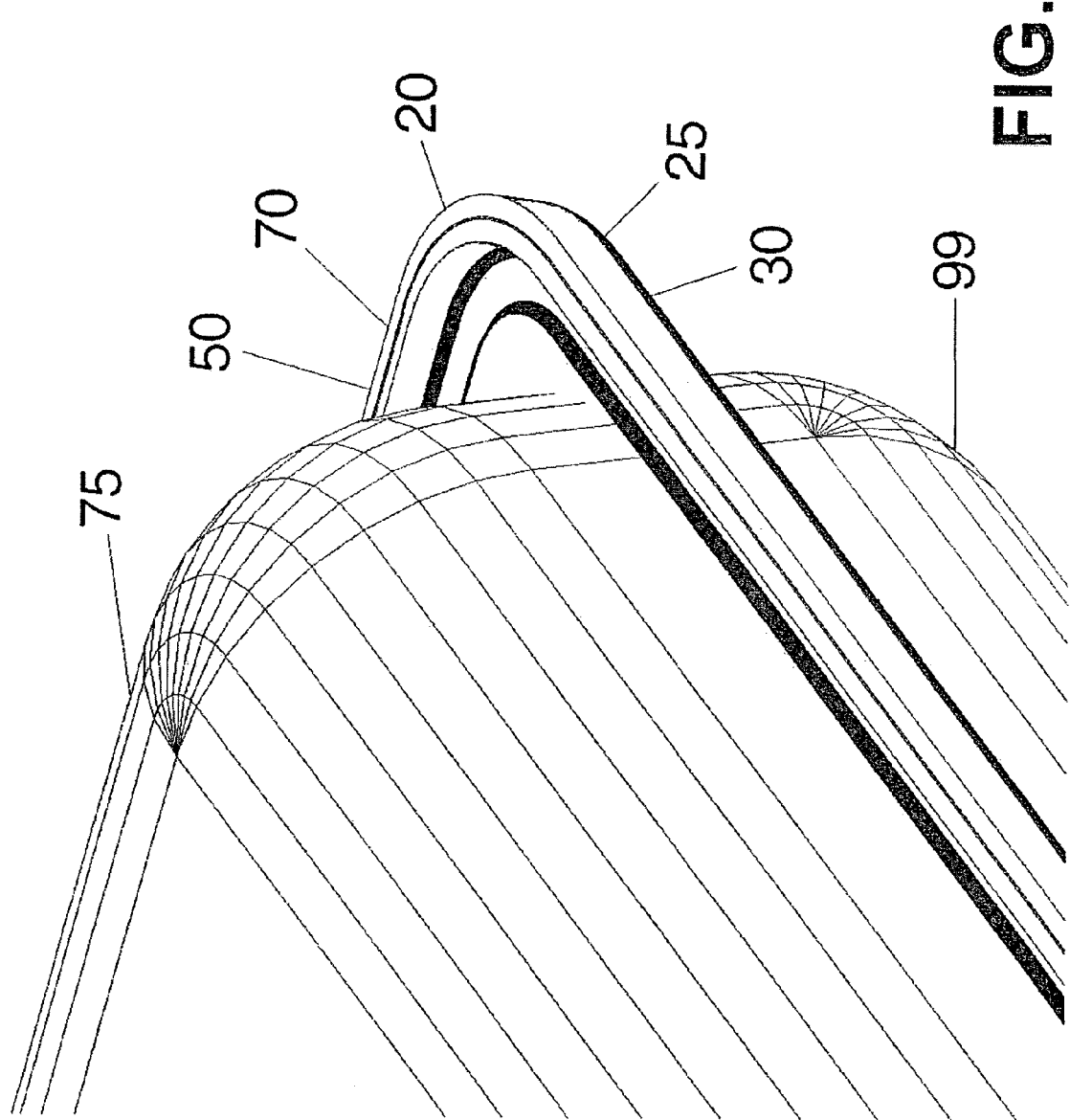
FIG. 4 is a side perspective view of one preferred embodiment of the thermal pack of the invention, featuring details of the bent lip design.

As shown in the preferred embodiment of FIG. 3, the thermal pack of the present invention 99 includes a first outer layer 50 and a second skin-side layer 70. The respective layers 50, 70 are sealed together substantially along peripheral edges to form an enclosed compartment or "bubble" 75 containing thermal (cold/heat-retaining) material (not shown in FIG. 3). As shown in FIG. 4, the sealed peripheral edges are formed into a "bent lip" configuration 30 having a smooth lower bend 25 along the skin side 70 and an upward-angled peripheral edge 20 along the outer side 50. The "bent lip" configuration in illustrated over the entire periphery, however, it is effective only in the area of skin contact. As such, sections of the periphery not likely to contact the skin need not include the bend. The thermal pack 99 is preferably provided with an attachment means 55 for selectively attaching the thermal pack 99 to a wrap 90 (FIGS. 3, 5 and 6). The attachment means 55 is preferably a hook or loop fastener, but may consist of a snap, button, clip or other selectively reusable fastener.

The thermal material 10 may be ice or gel based, and of the type conventionally used in prior art thermal packs. In a preferred embodiment, the thermal material consists of an alkane mixture similar to the type used in U.S. Pat. No. 6,185,742.

FIG. 5 provides a cross-section view showing further details of a preferred embodiment of the invention, including: a thermal pack 99 consisting of an inside ("skin side") layer of plastic material 70 that makes up the pack; an outside ("wrap side") layer of plastic material 50 that makes up the pack; the thermal material 10 captured in the enclosed compartment or bubble 75 formed between layers 70 and 50; a peripheral "bent lip" 30 formed when layers 70 and 50 are sealed together; a peripheral edge 20 created at the end of lip 30; means of attaching 55 the pack to an insulated wrap 90 (in this case, "hook" tabs); an insulated wrap 90 having a first or "pack" side 92 that is made of matching "loop" fasteners (for attaching the wrap 90 to the pack 99), and a second or opposite side 94 consisting of insulating material (e.g. neoprene). Directional arrow 95 indicates the attachment point of insulating wrap 90 to the "hook" tab 55 attachment means of the thermal pack 99.

FIG. 6 shows the components of the present invention assembled for use, including: a cooling pack 99 consisting of an inside "skin side" layer 70 of plastic material that makes up the pack; an outside ("wrap side") layer 50 of plastic material that makes up the pack; thermal material 10 captured with the bubble 75 formed between layers 50 and 70; the peripheral "bent lip" 30 formed by sealing layers 70 and 50; the peripheral edge 20 created at the end of the lip 30; attachment means 55 for attaching the pack to the insulated wrap 90 (in this case, "hook" tabs); the insulated wrap 90 having one side 92 that is made of matching "loop" fasteners (for attaching the wrap 90 to the pack 99), and its opposite side consisting of insulating material 94 (e.g. neoprene). FIG. 6 also shows the thermal pack in use such that the smooth edge 25 of the "bent lip" design 30 rests against the skin of the user, while the peripheral edge 20 points away from the user's skin 21.

FIGS. 5 and 6 include a schematic view of thermal energy transfer 105 from the user to the pack or the pack to user, depending upon the application. FIG. 5 also shows internal reflection of thermal energy 110 provided by an insulated layer 94 of the wrap 90, as well as external reflection of environmental thermal energy 115 that the insulated layer 94 of the wrap 90 produces.

Figure 7:
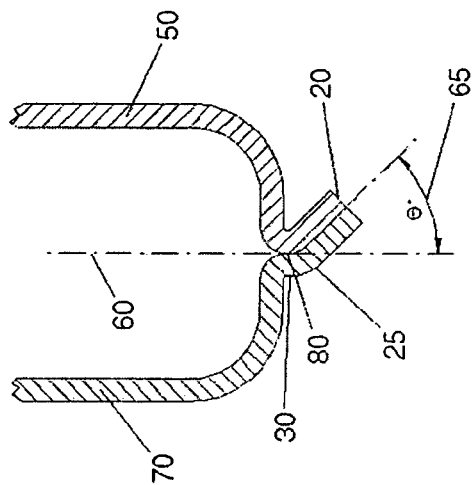
FIG. 7 is a side cross-section view of one preferred configuration of the bent lip design of the invention.
Figure 8:
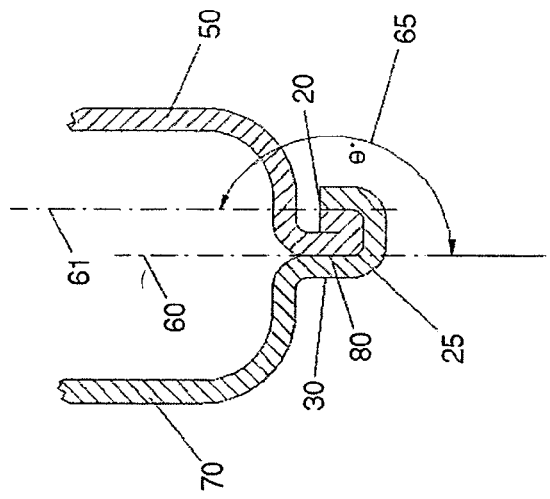
FIG. 8 is a side cross-section view of one preferred configuration of the bent lip design of the invention.
Figure 9:
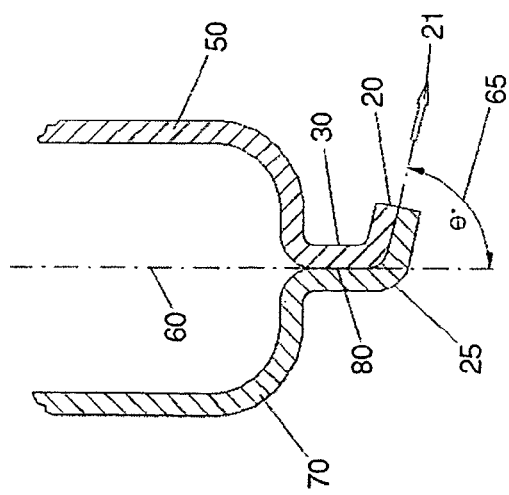
FIG. 9 is a side cross-section view of one preferred configuration of the bent lip design of the invention.

FIGS. 7-9 illustrate details of various preferred embodiments of the bent lip 30 feature of the invention. The bent lip 30 is created when layers 50, 70 are attached or welded together (e.g. by heat, chemical, or other process) to form a seal 80. When viewed along the horizontal sealing plane 60 formed by the seal 80, an angle θ (designated as item 65 in FIGS. 7-9) is created between the lip and horizontal sealing plane 60. This angle θ will be greater than 0 degrees when measured from horizontal sealing plane 60, indicated in FIG. 7. The bend is preferably created using a suitably configured die.

FIG. 8 shows an alternative embodiment of the invention in which the peripheral edge 20 is curled back upon itself, creating horizontal plane 61, which is substantially parallel to horizontal plane 60. In the configuration shown in FIG. 8, angle θ is about 180 degrees relative to the horizontal sealing plane 60. Optionally, the edge 20 could be folded over again or rolled to make angle θ any angle over 0°.

FIG. 9 describes an alternate embodiment of the design in which angle θ begins at a minimal distance from seal 80, thereby maximizing the volume of the bubble 75. In this embodiment, angle θ is a small angle, such as 20 to 30 degrees.

Figure 10:
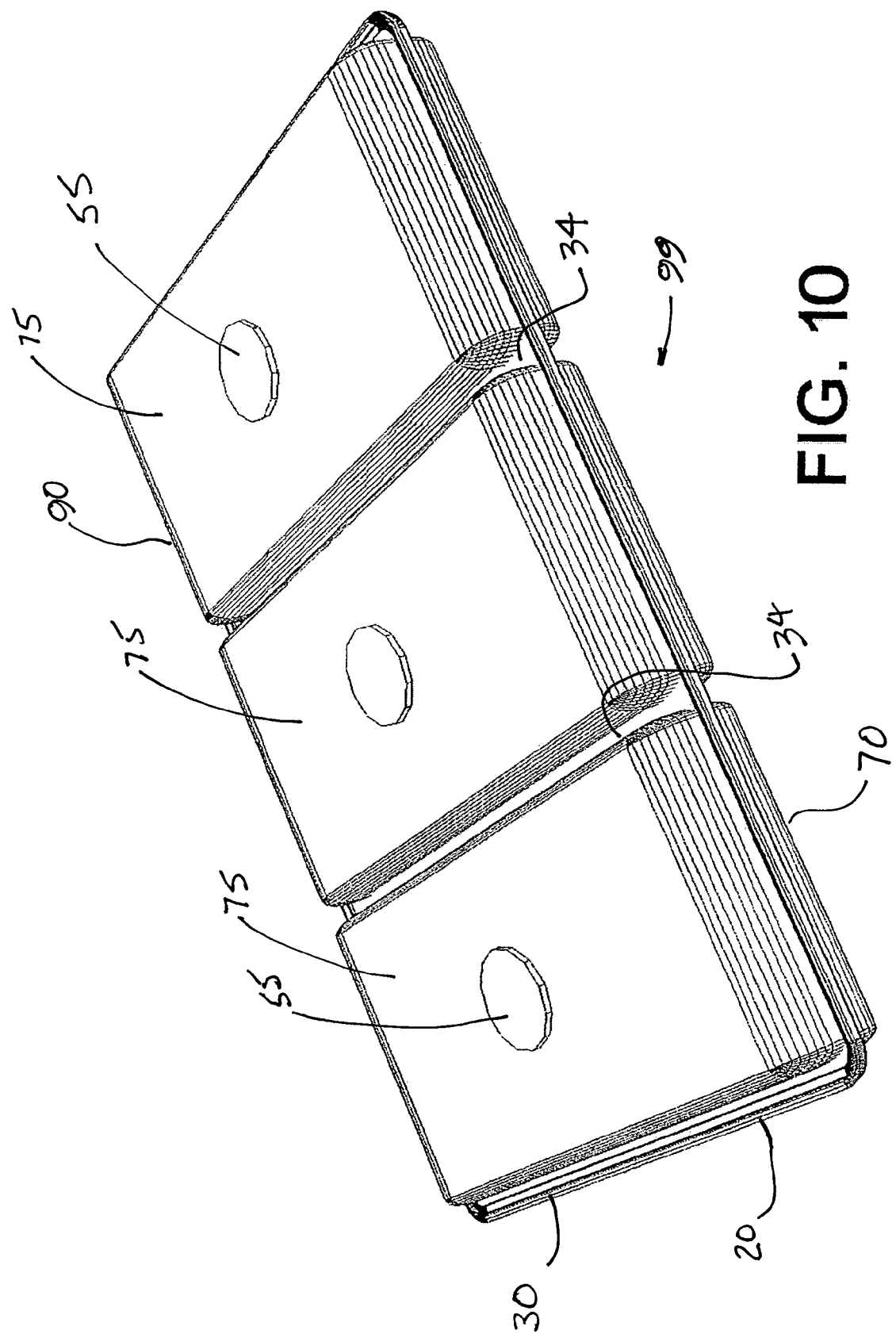
FIG. 10 is a side perspective view of one preferred embodiment of the invention incorporating a multi-segmented design.

As shown in FIG. 10, the thermal pack of the present invention can be provided with more than one "bubble" 75 such as by seal 34 joining the layers 70, 90 across the container 99. The bubbles may be arranged in various sizes or configurations in order to provide optimum ergonomic fit for the user. Additionally, a multiple compartment embodiment minimizes pooling of thermal fluid, as might occur, for example, in a large thermal pack.

FIGS. 11 through 13 illustrate an alternative to the embodiment of FIG. 10 wherein the thermal pack 99 is formed of a pliable material and the respective layers 50 and 70 are joined by one of the lips 30 described above, and a compartment or bubble effect is created by attaching the respective layers 50, 70 as by buttons 35 which are formed by welding, chemical or mechanical attachment as described above however intermediate throughout the container 75. The advantage of this embodiment is that the overall form or integrity of the pack 99 is retained, however the thermal material 10 (not shown) is not confined to a particular container or bubble 75 (as illustrated in FIG. 10).

Although the present invention has been described in terms of specific embodiments, it is anticipated that alterations and modifications thereof will no doubt become apparent to those skilled in the art. It is therefore intended that the following claims be interpreted as covering all alterations and modifications that fall within the true spirit and scope of the invention.

What is claimed is:

1. A thermal pack for avoiding irritation of the skin of a user comprising: a thermoplastic container forming an enclosed compartment having a skin side and a distal side, said sides meeting at a periphery of the container thereby enclosing the compartment, said compartment containing a thermal component, and said container periphery having a lip extending in a plane outwardly of the periphery, said lip fixedly formed such that a distal end of said lip extends angularly away from the plane of the periphery by an angle of at least about 20° and at most about 90° from said skin side of said compartment to thereby prevent said distal end of said lip from coming into contact with the user wherein the distal side includes attachment means for attaching a wrap for covering the distal side of the pack.

2. The thermal pack of claim 1 wherein the peripheral lip is bent to an angle exceeding about 45 degrees from the plane of the periphery.

3. The thermal pack of claim 1 wherein the attachment means is one of a hook and loop, a nap, a button and a clip fastener.

* * * * *